(12) United States Patent
Chen

(10) Patent No.: US 9,497,998 B2
(45) Date of Patent: Nov. 22, 2016

(54) ELECTRONIC CIGARETTE

(71) Applicant: SHENZHEN SMOORE TECHNOLOGY LIMITED, Shenzhen (CN)

(72) Inventor: Zhiping Chen, Shenzhen (CN)

(73) Assignee: Shenzhen Smoore Technology Limited, Shenzhen (CN)

( * ) Notice: Subject to any disclaimer, the term of this patent is extended or adjusted under 35 U.S.C. 154(b) by 450 days.

(21) Appl. No.: 14/240,073

(22) PCT Filed: Dec. 3, 2013

(86) PCT No.: PCT/CN2013/088386
§ 371 (c)(1),
(2) Date: Feb. 21, 2014

(87) PCT Pub. No.: WO2015/081483
PCT Pub. Date: Jun. 11, 2015

(65) Prior Publication Data
US 2015/0150306 A1    Jun. 4, 2015

(51) Int. Cl.
A24F 47/00 (2006.01)
H05B 1/02 (2006.01)
H05B 3/40 (2006.01)
A61M 15/06 (2006.01)

(52) U.S. Cl.
CPC .............. *A24F 47/008* (2013.01); *H05B 3/40* (2013.01); *A61M 15/06* (2013.01)

(58) Field of Classification Search
CPC .. A24F 47/008; A24F 47/002; A61M 15/06; H05B 3/40
See application file for complete search history.

(56) References Cited

U.S. PATENT DOCUMENTS

| | | | | |
|---|---|---|---|---|
| 2014/0196734 A1* | 7/2014 | Liu | ........................ | A24F 47/008 131/329 |
| 2014/0348495 A1* | 11/2014 | Greim | ..................... | H05B 3/02 392/386 |
| 2014/0360514 A1* | 12/2014 | Zhu | ........................ | A24F 47/008 131/329 |
| 2014/0366895 A1* | 12/2014 | Li | ....................... | H01M 2/1055 131/329 |
| 2015/0007835 A1* | 1/2015 | Liu | ........................ | A24F 47/008 131/329 |

FOREIGN PATENT DOCUMENTS

| | | | |
|---|---|---|---|
| CN | 201499601 U | * | 6/2010 |
| CN | 101843368 A | * | 9/2010 |
| CN | 203194539 U | * | 9/2013 |

OTHER PUBLICATIONS

International Search Report, Sep. 4, 2014.*

* cited by examiner

*Primary Examiner* — Michael J Felton
*Assistant Examiner* — Jerzi H Moreno Hernandez
(74) *Attorney, Agent, or Firm* — Coats & Bennett, P.L.L.C.

(57) ABSTRACT

An electronic cigarette includes a mouthpiece, an atomizer assembly, a first connecting assembly, a second connecting assembly, and a power assembly. The atomizer assembly is received in the first housing of the mouthpiece, which includes a liquid reservoir and a heating element. The first connecting assembly includes a first conductive tube, a second conductive tube, and a first sleeve. The first sleeve includes an insulation tube, a convex ring, and a connecting portion. The insulation tube is disposed between the first conductive tube and the second conductive tube; the convex ring is sleeved on the second conductive tube and fixed to the first housing; the connecting portion extends through the second conductive tube and interconnects the insulation tube and the convex ring. The second connecting assembly includes a second sleeve and a flexible conductive ring. The power assembly includes a second housing fixed to the first housing and a battery.

16 Claims, 11 Drawing Sheets

ELECTRONIC CIGARETTE

FIELD OF THE INVENTION

The present disclosure relates to electronic cigarette.

BACKGROUND OF THE INVENTION

It is well known that smoking is harmful to health. Electronic cigarettes contain less harmful ingredients than conventional cigarettes, thus more and more people prefer electronic cigarettes over conventional cigarettes.

An atomizer assembly and a power assembly of a conventional electronic cigarette are connected together by using magnet, the deformation of rubber component, or wire. In the connection method of using magnet, a magnet is usually embedded in one of the atomizer assembly and the power assembly; and the other is made of stainless steel, thus the atomizer assembly and the power assembly are attracted to each other to be connected together. The magnet according to this method can easily be ineffective at high temperature. In the connection method of using the deformation of rubber component, the structural stability of the components is poor due to the abrasion or high temperature, which will cause a leakage problem or a contact failure. In the connection method of using wire, a contact failure is easily caused, which will greatly reduce the service life of the electronic cigarette.

SUMMARY OF THE DISCLOSURE

This section provides a general summary of the disclosure, and is not a comprehensive disclosure of its full scope or all of its features.

The present disclosure is directed to an electronic cigarette having a better structural stability and a long service life.

An electronic cigarette includes a mouthpiece, an atomizer assembly, a first connecting assembly, a second connecting assembly, and a power assembly. The mouthpiece has a first housing. The first housing defines an air passage therein. The atomizer assembly is received in the first housing and includes a liquid reservoir and a heating element. The liquid reservoir surrounds the heating element. The first connecting assembly is received in the first housing. The first connecting assembly includes a first conductive tube, a second conductive tube connected to the heating element, and a first sleeve. The second conductive tube is sleeved on the first conductive tube. The first sleeve includes an insulation tube, a convex ring, and a connecting portion. The insulation tube is disposed between the first conductive tube and the second conductive tube. The convex ring is sleeved on the second conductive tube and fixed to an inner wall of the first housing. The connecting portion extends through a wall of the second conductive tube and interconnects the insulation tube and the convex ring. The convex ring and the second conductive tube define a receiving groove therebetween. The second connecting assembly includes a second sleeve, and a flexible conductive ring. The second sleeve is conductive and includes a body and a boss protruding from the body. The boss is received in the receiving groove. The flexible conductive ring is sleeved on the second conductive tube, the flexible conductive ring includes a clamping end and a contact end connected to the clamping end. The clamping end abuts against an inner wall of the second sleeve. The contact end includes a plurality of resilient contacts, and the second conductive tube is clamped by ends of the resilient contacts. The power assembly includes a second housing and a battery received in the second housing. The second housing is fixed to the first housing. An end of the battery is electrically connected to the second sleeve; the other end of the battery is electrically connected to the first conductive tube.

The first conductive tube and the second conductive tube of the first connecting assembly of the electronic cigarette are used as positive and negative electrodes, respectively. The first conductive tube and the second conductive tube are insulated and connected by the first sleeve, and the first sleeve is fixed to the first housing to form a stable structure. The second sleeve and the second conductive tube are electrically connected by the flexible conductive ring, therefore the contact area between the flexible conductive ring and the second sleeve becomes larger, and the contact area between the flexible conductive ring and the second conductive tube is larger. The contact failure is avoided due the flexible connection. The first housing and the second housing used for receiving various internal components are fixed together to form a stable structure. In other words, the various components of the electronic cigarette are mutually cooperated with each other. The electronic cigarette is not susceptible to environmental variation, and it has a high reliability; thus the electronic cigarette has a long service life.

Further areas of applicability will become apparent from the description provided herein. The description and specific examples in this summary are intended for purpose of illustration only and are not intended to limit the scope of the present disclosure.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION OF THE EMBODIMENTS

Illustrative embodiments of the disclosure are described below. The following explanation provides specific details for a thorough understanding of and enabling description for these embodiments. One skilled in the art will understand that the disclosure may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein,""above," "below" and words of similar import, when used in this application, shall refer to this application as a whole and not to any particular parts of this application. When the claims use the word "or" in reference to a list of two or more items, that word covers all of the following interpretations of the word: any of the items in the list, all of the items in the list and any combination of the items in the list.

Figure 1:
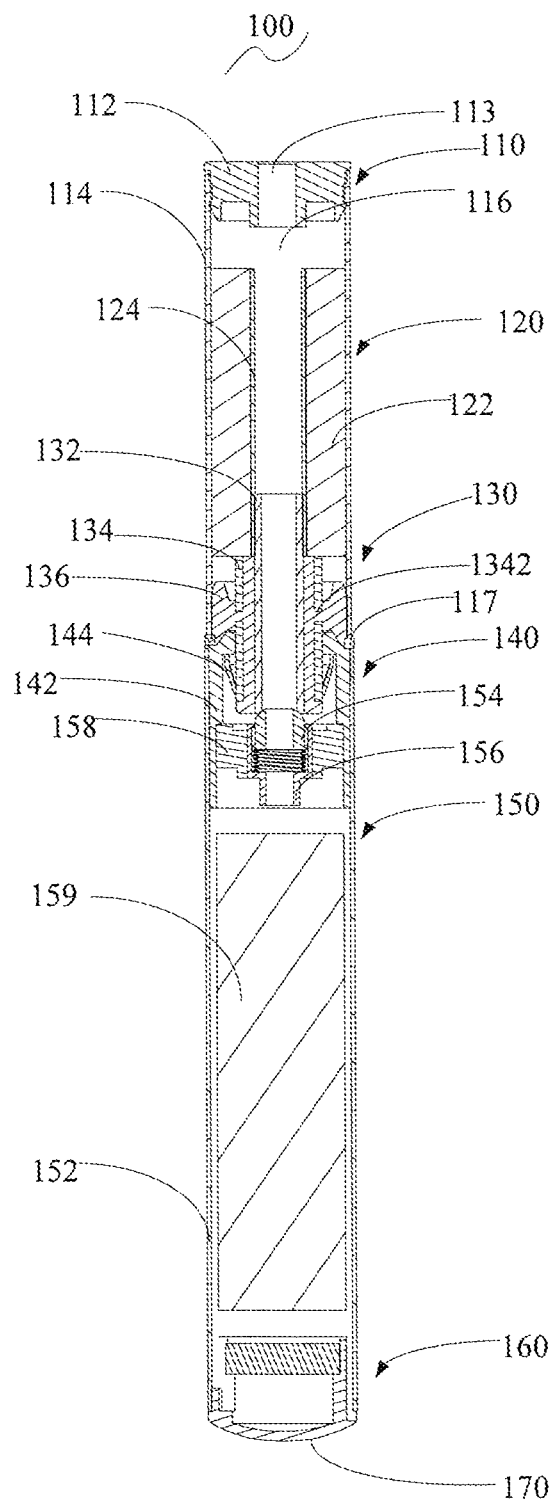
FIG. 1 is a cross-sectional view of an embodiment of an electronic cigarette.
Figure 2:
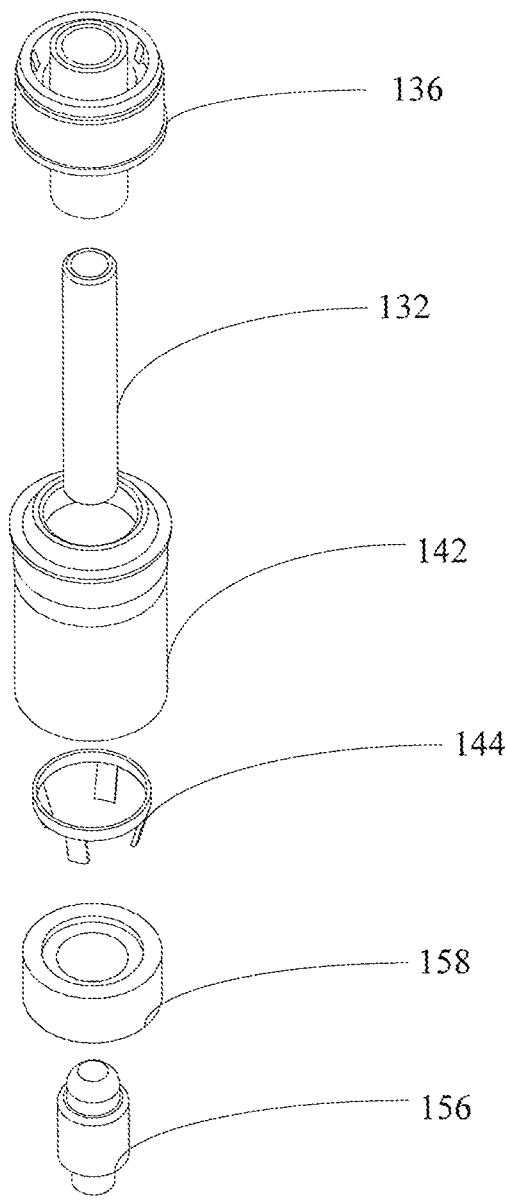
FIG. 2 is a partial, exploded perspective view of the electronic cigarette shown in FIG. 1.

Referring to FIG. 1 and FIG. 2, an embodiment of an electronic cigarette 100 includes a mouthpiece 110, an atomizer assembly 120, a first connecting assembly 130, a second connecting assembly 140, a power assembly 150, a controller 160 and a base cover 170, which are connected in that order. In the illustrated embodiment, the electronic cigarette 100 is approximately shaped as a cylinder. Alternatively, the electronic cigarette 100 may have a shape of a prism and so on.

The mouthpiece 110 includes a mouthpiece cover 112 and a first housing 114 connected to the mouthpiece cover 112. The mouthpiece cover 112 is made of plastic, preferably silicone. The mouthpiece cover 112 defines an air outlet 113 for air flow getting out. The base cover 170 defines an air intake (not shown) for air flow entering. The electronic cigarette 100 forms an air passage 116 therein communicated with the air intake and the air outlet 113. The air can enter the electronic cigarette 100 from the air intake of the base cover 170 and get out from the air outlet 113 with smoke for users to inhale. Partial air passage 116 is disposed in the first housing 114. The air passage 116 can be formed by a hollow pipeline in the atomizer assembly 120, or it can be formed by a wall of the atomizer assembly 120 and a wall of the first housing 114 defining a space therebetween.

Figure 3:
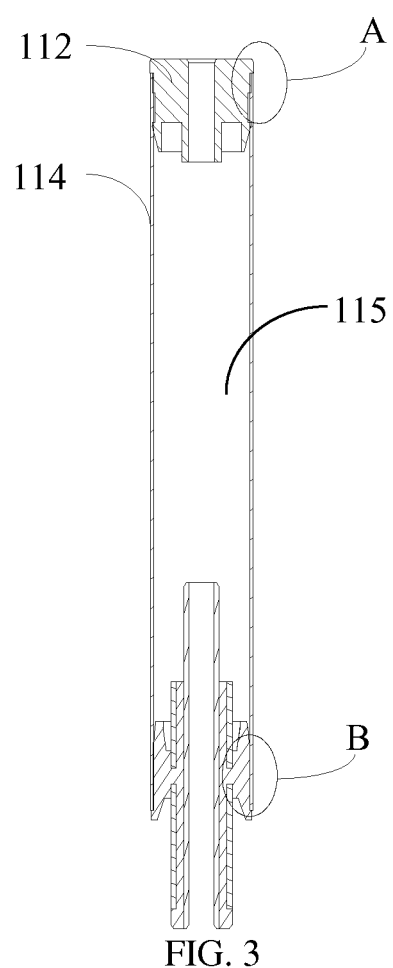
FIG. 3 is a partial, cross-sectional view of the electronic cigarette shown in FIG. 1.
Figure 4:
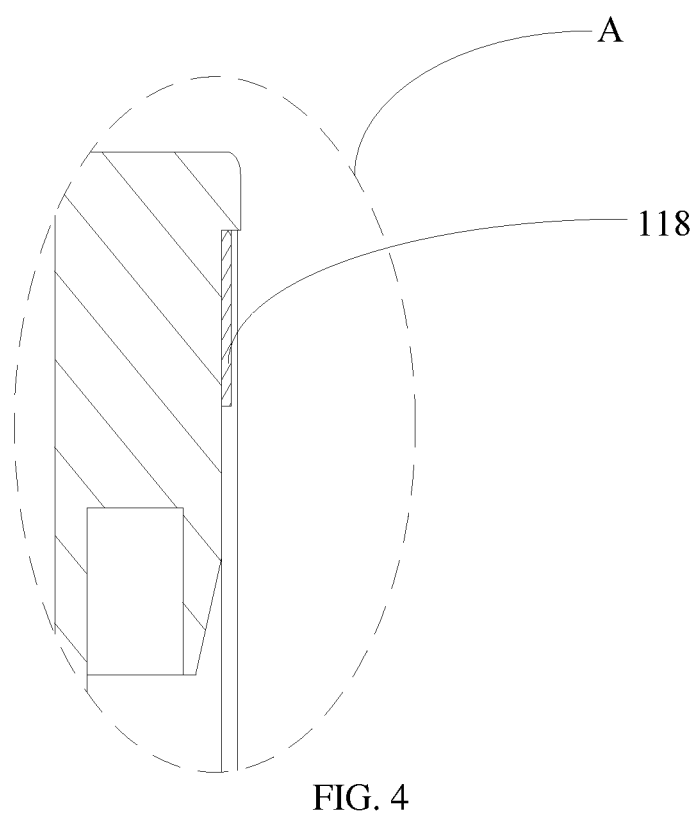
FIG. 4 is an enlarged, cross-sectional view of A shown in FIG. 3.

Referring to FIG. 3, the first housing 114 has a cavity 115 for receiving part of the internal components of the electronic cigarette 100, such as the atomizer assembly 120, the first connecting assembly 130 and so on. The power assembly 150 includes a second housing 152 and various internal components received in the second housing 152. The first housing 114 is fixed to the second housing 152. Specifically, the first housing 114 is tightly connected to the second housing 152 by a first weld ring 117, which is formed by laser welding. Laser welding is a high-precision welding method using the laser beam with a high energy density as a heat source. It has been successfully applied to the precision welding of the micro and small parts due to its unique advantages. Referring to FIG. 3 and FIG. 4, in one embodiment, in order to prevent the leakage of smoke, a second weld ring 118 formed by the laser welding is provided between the mouthpiece cover 112 and the first housing 114. The second weld ring 118 is sleeved on the mouthpiece cover 112. The mouthpiece cover 112 is tightly connected to the first housing 114 by the second weld ring 118.

Figure 5:
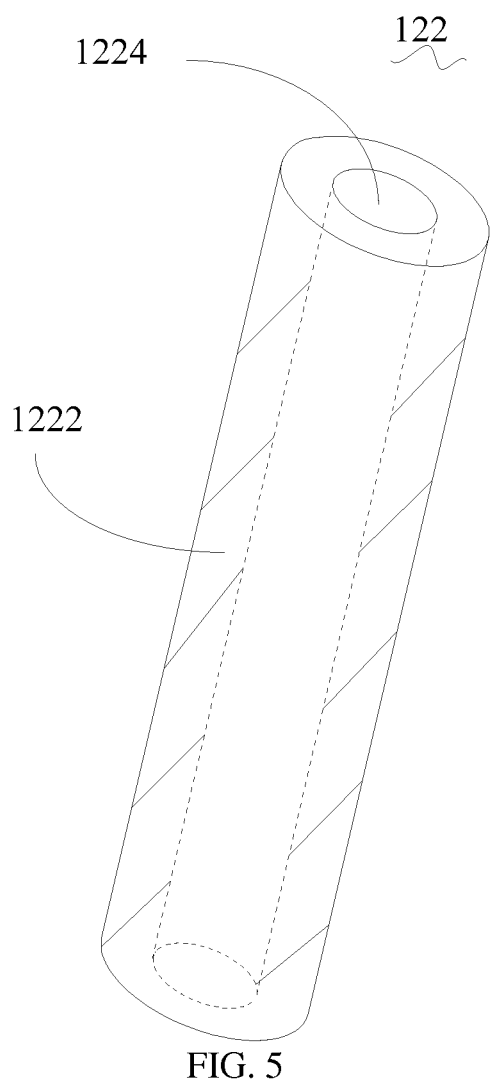
FIG. 5 is a perspective view of an embodiment of a liquid reservoir.
Figure 6:
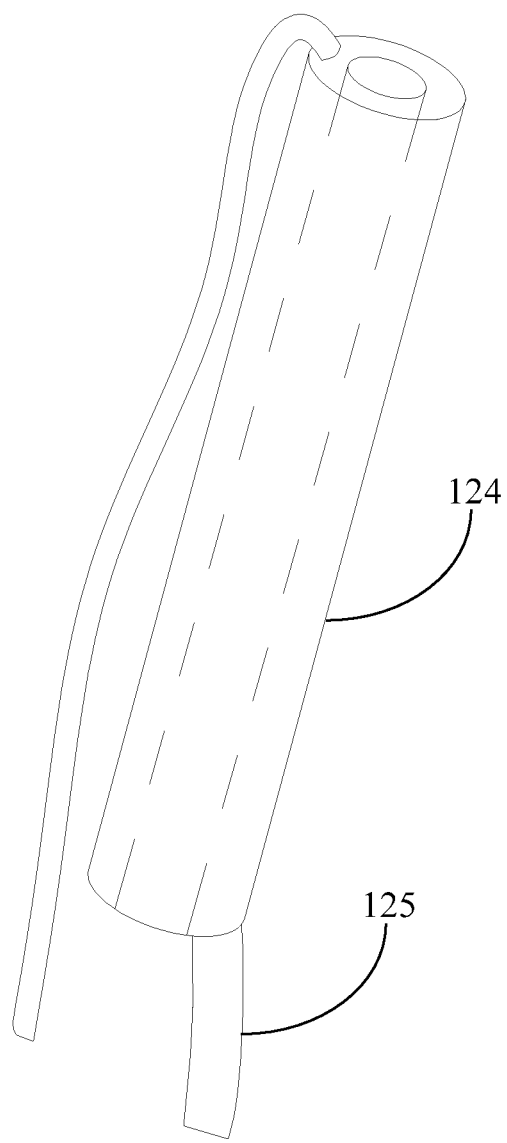
FIG. 6 is a perspective view of an embodiment of a heating element.

Referring to FIG. 1, the atomizer assembly 120 is received in the cavity 115 of the first housing 114. The atomizer assembly 120 includes a liquid reservoir 122 and a heating element 124 being in contact with the liquid reservoir 122. Referring to FIG. 5, the liquid reservoir 122 is a hollow tube. In one embodiment, the liquid reservoir 122 includes a liquid medium 1222 and a receiving channel 1224 formed in the inside of the liquid medium 1222. The liquid medium 1222 is made of fibers and the like, such as a heating resistant fiber. Preferably, the liquid medium 1222 is made of a modified fiber, which is used to remove an unpleasant taste of the liquid medium 1222. The heating element 124 is received in the receiving channel 1224, and at least partial surface of the heating element 124 is in contact with the liquid medium 1222, thus the liquid stored in the liquid reservoir 122 can be transferred to the heating element 124. Specifically, referring to FIG. 6, the heating element 124 is a heating tube capable of absorbing and heating liquid. A pipeline of the heating tube forms part of the air passage 116. The heating tube is provided with two wires 125 on the two ends thereof. An outside diameter of the heating tube substantially equals to the diameter of the receiving channel 1224, at least partial outer surface of the heating tube is in contact with the inner surface of the liquid medium 1222. Since the heating tube has a capacity of absorbing liquid and heating, the liquid stored in the liquid reservoir 122 can be transferred to the heating tube by capillary action, and the liquid can be uniformly heated to form uniformly atomized particles by the heating tube. Using the heating tube as the heating element 124, the heating element 124 has a larger absorbing area and heating area; the speed of the atomization is accelerated.

Figure 7:
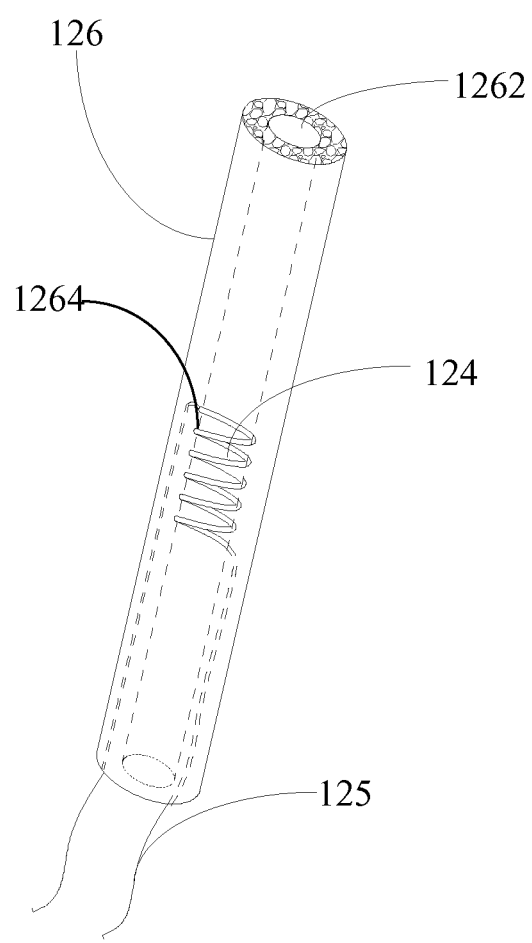
FIG. 7 is a perspective view of another embodiment of a heating element.

Alternatively, referring to FIG. 7, the atomizer assembly 120 further includes a conducting liquid tube 126 between the liquid reservoir 122 and the heating element 124. The conducting liquid tube 126 is received in the receiving channel 1224. An outside diameter of the conducting liquid tube 126 substantially equals to the diameter of the receiving channel 1224, thus the conducting liquid tube 126 is in contact with liquid medium 1222. The conducting liquid tube 126 has a pipeline 1262 therein for receiving the heating element 124. The conducting liquid tube 126 is made of rigid porous materials capable of storing liquid and temperature resistance, such as silicone, porous ceramics, etc. Since the conducting liquid tube 126 has excellent capacity of absorbing liquid, it can absorb the liquid stored in the liquid reservoir 122.

In one embodiment, the heating element 124 is the heating tube capable of absorbing liquid and heating liquid, the heating tube is received in the pipeline 1262, and at least partial surface of the heating tube is in contact with the conducting liquid tube 126. Alternatively, the heating element 124 is a spiral heating coil; the spiral direction of the heating coil is the same as the direction of the pipeline 1262. The conventional heating coil is usually laterally disposed in the air passage of the electronic cigarette, the diameter of the air passage is relatively small, thus only a few heating coil can be configured. While in this technical solution, the spiral direction of the heating coil is the same as the direction of the pipeline 1262. The number of the heating coil can be significantly increased comparing to the conventional heating coil. In which, the diameter of the heating coil substantially equals to the inner diameter of the pipeline 1262, thus the outer surface of the heating coil is in contact with the inner wall of the conducting liquid tube 126. The heating coil is made of conductive material, such as metal or alloy; preferably, nickel-chromium alloy wire. The heating coil is resilient, the conducting liquid tube 126 is made of rigid material, thus heating coil can be directly fixed to the pipeline 1262 of the conducting liquid tube 126 without the help of any supporter, the structure is simplified. The heating coil is provided with two wires 125 on the two ends thereof to connect to the electric conductor.

Furthermore, referring to FIG. 7, the conducting liquid tube 126 defines a groove 1264 with a shape adapting to the heating coil on the inner wall thereof. The heating coil is received in the groove 1264; partial surface of the heating coil is exposed in the air in the pipeline 1262. The heating coil can be tightly fixed to the conducting liquid tube 126 due to the groove 1264. The contact area between the heating coil and the conducting liquid tube 126 is enlarged, thus the atomization is improved. Moreover, the heating coil is used as the heating element 124, the space for air-flowing in the pipeline is enlarged; the gas flux is enhanced. The heating element 124 and the conducting liquid tube 126 can be formed by one-piece injection molding. The installation process is simplified, and the structural stability is excellent.

Figure 8:
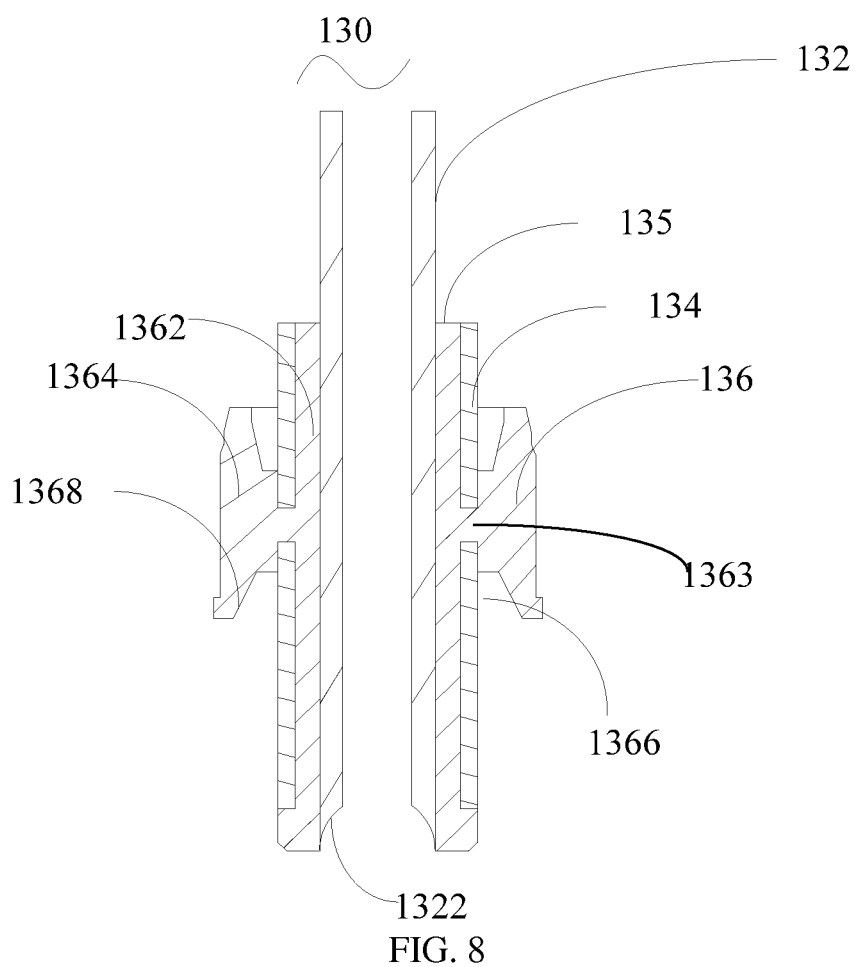
FIG. 8 is a partial, cross-sectional view of the first connecting assembly shown in FIG. 1.

The first connecting assembly 130 and the second connecting assembly 140 are mutually cooperated to each other to form a stable structure. Referring to FIG. 8, the first connecting assembly 130 includes a first conductive tube 132, a second conductive tube 134 and a first sleeve 136. The second conductive tube 134 is sleeved on the first conductive tube 132 and is not in direct contact with the first conductive tube 132, i.e. the diameter of the second conductive tube 134 is greater than that of the first conductive tube 132. The length of the second conductive tube 134 is greater than that of the first conductive tube 132; an end of the second conductive tube 134 and an end of the first sleeve 136 cooperatively form a flange 135, which is used to support the atomizer assembly 120. Referring to FIG. 1, the second conductive tube 134 defines two through holes 1342 on the wall thereof aligned to each other. In one embodiment, the central axis of the first conductive tube 132 and the central axis of the second conductive tube 134 coincide with each other, thus the stability of this structure is much better. The first conductive tube 132 and the second conductive tube 134 are made of conductive material, preferably, metals. One end of first conductive tube 132 and one end of the second conductive tube 134 are connected to two wires 125 of the heating element 124, respectively; the other end of first conductive tube 132 and the other end of the second conductive tube 134 are respectively connected to the power assembly 150 to form the positive and negative electrodes. The first conductive tube 132 and the second conductive tube 134 are insulated with each other by the first sleeve 136. Preferably, in order to ensure the first conductive tube 132 is tightly connected to the power supply assembly 150, the first conductive tube 132 has an inwardly concave surface 1322 on an end thereof to enlarge the contact area between the first conductive tube 132 and the corresponding element of the power supply assembly 150.

Figure 9:
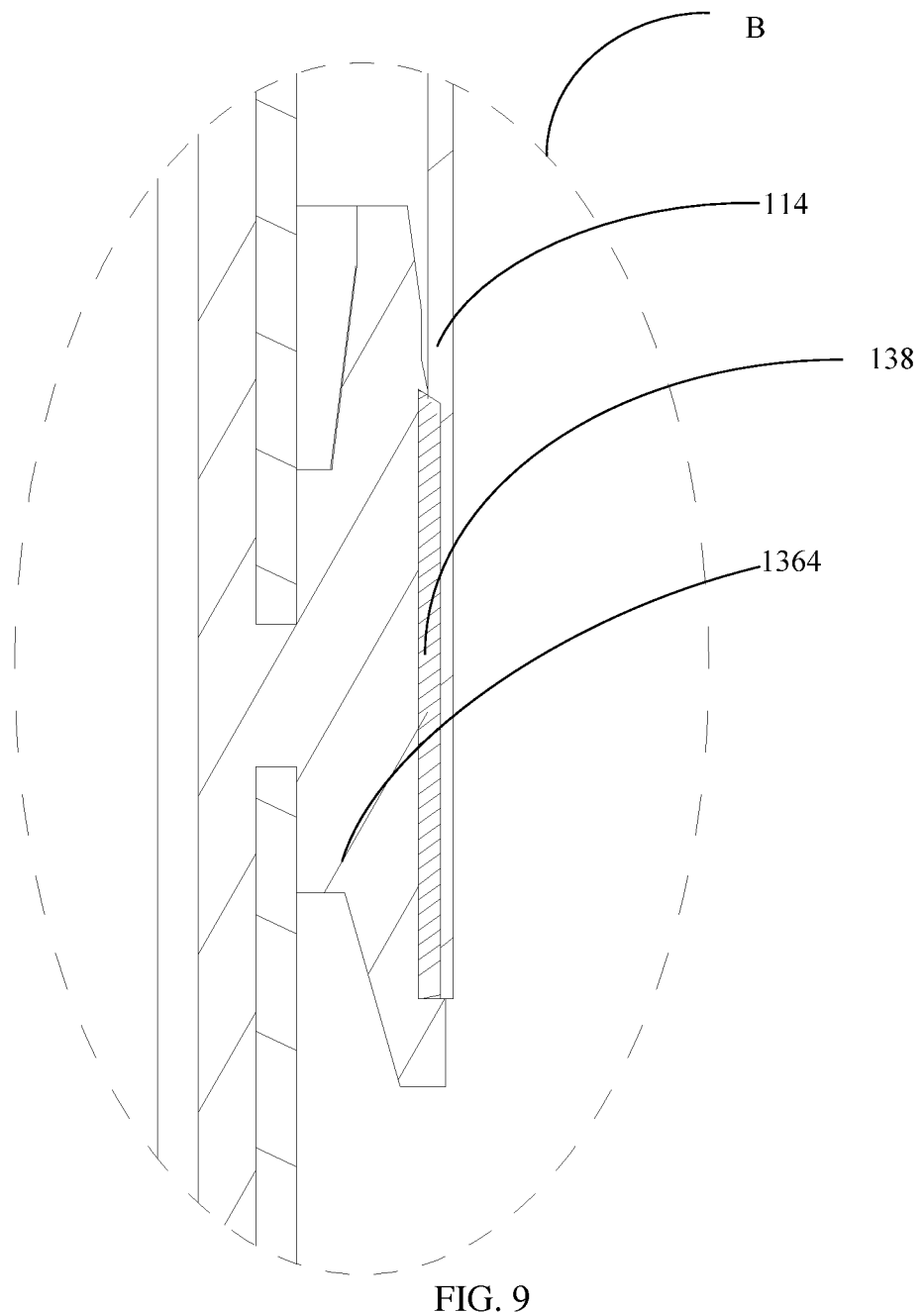
FIG. 9 is an enlarged, cross-sectional view of B shown in FIG. 3.

The first sleeve 136 includes an insulation tube 1362, a connecting rod 1363, and a convex ring 1364. The insulation tube 1362 is disposed between the first conductive tube 132 and the second conductive tube 134. Preferably, the insulation tube 1362 is in contact with the outer wall of the first conductive tube 132 and the inner wall of the second conductive tube 134 to ensure the first conductive tube 132 is tightly connected to the second conductive tube 134. The connecting rod 1363 extends through the through hole 1342 of the second conductive tube 134 to connect the insulation tube 1362 and the convex ring 1364. The convex ring 1364 is received in the cavity 115 of the first housing 114. The outer wall of the convex ring 1364 is in contact with the inner wall of the first housing 114. The contact area between the convex ring 1364 and the first housing 114 is great, which can make the convex ring 1364 to be much tightly fixed to the first housing 114. Furthermore, in one embodiment, referring to FIG. 9, the convex ring 1364 is tightly fixed to the first housing 114 by a third weld ring 138 formed by laser welding. The convex ring 134 and the second conductive tube 134 define a receiving groove 1366 therebetween for receiving the second connecting assembly 140. The convex ring 1364 has a first correction slope 1368 to be better cooperated with the second connecting assembly 140. Proceeding from the above, the first sleeve 136 is tightly fixed to the first housing 114, and tightly cooperated with the second conductive tube 134 and the first conductive tube 132 one another; thus a better structural stability is obtained. Preferably, the first sleeve 136 is made of insulating materials, preferably plastic, which is easy to fabricate. The first conductive tubes 132, the second conductive tube 134 and the first sleeve 136 can be integrally formed by injection molding. Preferably, a certain portion of fluxing agent is added to the insulating material before the injection molding, which is beneficial for the first sleeve 136 being welded to the first housing 114. The process of injection molding by using a mold is simple, and the overall stability of the first conductive tube 132, the second conductive tube 134 and the first sleeve 136 is excellent. The first conductive tube 132 and the second conductive tube 134 are spaced by the first sleeve 136, which prevents the contact of the positive electrode and negative electrode to short circuit.

Figure 10:
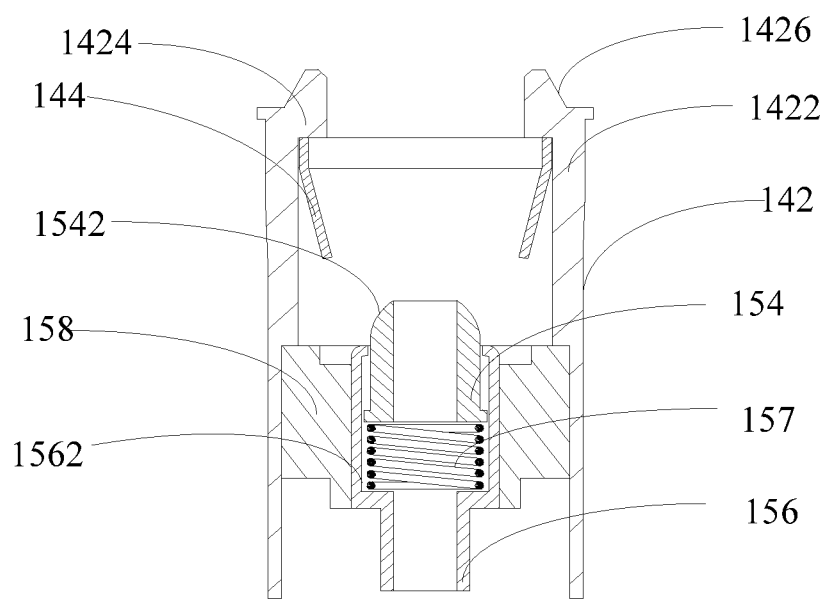
FIG. 10 is a partial, cross-sectional view of the electronic cigarette shown in FIG. 1.

Referring to FIG. 10, the second connecting assembly 140 includes a second sleeve 142 and a flexible conductive ring 144. The second sleeve 142 is made of conductive materials. The second sleeve 142 includes a body 1422 and a boss 1424 connected to the body 1422. The shape of the boss 1424 is adapted with the shape of the convex ring 1364. The boss 1424 is received in the receiving groove 1366 formed by the convex ring 1364 and the second conductive tube 134, and a central axis of the first sleeve 136 and that of the second sleeve 142 coincide with each other; thus the structural stability of the first sleeve 136 and second sleeve 142 is great. Preferably, the boss 1424 has a second correction slope 1426 on an end thereof. The second correction slope 1426 is completely in contact with the first correction slope 1368 to form a surface-to-surface contact, thus the boss 1424 can be better cooperated with the convex ring 1364.

Figure 11:
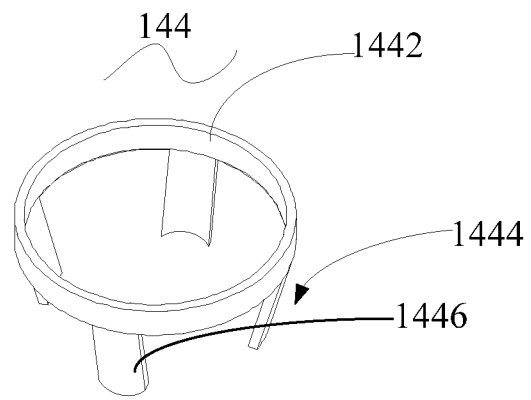
FIG. 11 is a perspective view of an embodiment of a flexible conductive ring.

Referring to FIG. 10 and FIG. 11, the flexible conductive ring 144 is substantially annular. The flexible conductive ring 144 is made of metal, preferably, alloy. The flexible conductive ring 144 includes a clamping end 1442 and a contact end 1444 connected to the clamping end 1442. The shape of the clamping end 1442 is the same as that of the body 1422 of the second sleeve 142, and the outer diameter of the clamping end 1442 approximately equals to the inner diameter of body 1422. The clamping end 1442 is received in the second sleeve 142. The clamping end 1442 resiliently abuts against an inner wall of body 1422 of the second sleeve 142. The clamping end 1442 and the second sleeve 142 from a surface-to-surface contact, thus a larger contact area can be formed ensure a better connection between the electric conductors to avoid contact failure. Preferably, the top end of the clamping end 1442 abuts against the bottom of the second sleeve 1442 of the second sleeve 142. The contact end 1444 includes a plurality of resilient contacts 1446. Preferably, the plurality of resilient contacts 1446 are spaced apart from one another. Each resilient contact 1446 is inclined to an axis of the clamping end 1442, and a distance of the plurality of resilient contacts 1446 gradually decreases along the direction far away from the clamping end 1442. When the second conductive tube 134 extends through the flexible conductive ring 144, the plurality of inclined resilient contacts 1446 expand outwardly, thus the second conductive tube 134 is clamped between the resilient contacts 1446.

Figure 12:
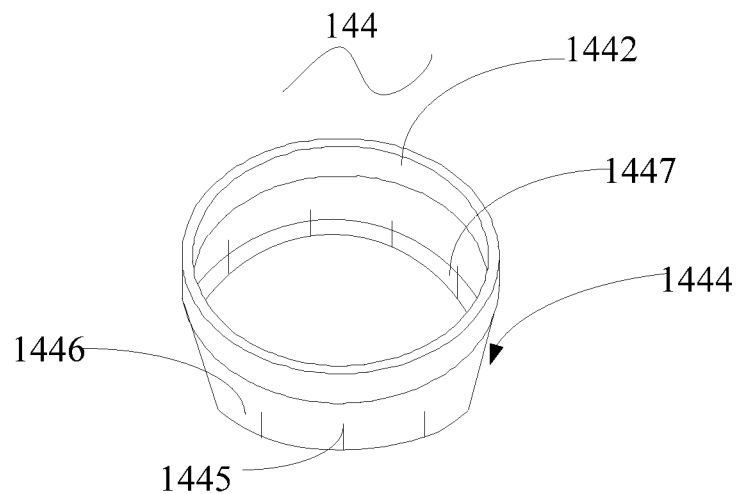
FIG. 12 is a perspective view of another embodiment of a flexible conductive ring.

Referring to FIG. 12, in an alternatively embodiment, the contact end 1444 is approximately is shaped as a horn, the plurality of resilient contacts 1446 are formed by a plurality of notch 1445 on the contact end 1444, The closer to the second conductive tube 134, the smaller the inner diameter of the contact end 1444. The resilient contacts 1446 have a concave surface 1447 on an end of abutting against the second conductive tube 134; the concave surface 1447 is in contact with the outer surface of the second conductive tube 134.

The contact area is great because the flexible conductive ring 144 and the second conductive tube 134, the flexible conductive ring 144 and the second sleeve 134 form surface-to-surface contacts. Besides, the flexible conductive ring 144 has a good elasticity, thus the flexible conductive ring 144 and the second conductive tube 134, the flexible conductive ring 144 and the second sleeve 142 are in excellent contact, which can be used as good electric conductors. Furthermore, the stability of the structure is great. In use, each component is not easy to loosen, thus the phenomenon of open circuit is avoided.

The power assembly 150 includes a second housing 152, an electrode head 154, an electrode holder 156, a spring 157, a fixing base 158, and a battery 159. The electrode head 154, the electrode holder 156, the spring 157, the fixing base 158, and the battery 159 are received in the second housing 152. Preferably, the battery 159 is a lithium battery which is rechargeable.

The power assembly 150 is fixed to the first housing 114. Specifically, the second housing 152 is fixed to the first housing 114 by the first weld ring 117, the connection is stable and not susceptible by the environment. The second housing 152 is made of conductive materials, preferably, metal.

Referring to FIG. 10, the electrode head 154 is hollow to form part of the air passage 116. An end of the electrode head 154 is connected to the first conductive tube 132; the other end of the electrode head 154 is received in the electrode holder 156. Preferably, the electrode head 154 has a convex surface 1542 on an end connected to the first conductive tube 132; the convex surface 1542 is in contact with the concave surface 1322 of the first conductive tube 132 to form a smooth surface-to-surface contact. The conductivity is good; the phenomenon of contact failure is avoided.

An end of the electrode holder 156 is connected to the electrode head 154; the other end is connected to the battery 159. Referring to FIG. 10, the diameter of the bottom of electrode holder 156 is smaller than that of the top of electrode holder 156; the electrode holder 156 forms a receiving groove 1562 therein for receiving the electrode head 154 and the spring 157. An end of the spring 157 abuts against the electrode head 154; the other end of the spring 157 is disposed on the bottom of the receiving groove 1562. The electrode head 154, the first conductive tube 132, and the electrode holder 156 are elastically connected by the spring 157; the phenomenon of contact failure is avoided.

The fixing base 158 is substantially shaped as a hollow cylinder. The fixing base 158 surrounds the outer wall of the electrode holder 156. The inner wall of the fixing base 158 is in contact with the outer wall of the electrode holder 156, thus the electrode holder 156 is fixed in the fixing base 158. An outer wall of the fixing base 158 is fixed to the inner wall of the second sleeve 142. Preferably, the fixing base 158 is fixed to the second sleeve 142 by laser welding to form a tightly connection.

The controller 160 is received in the second housing 152, which is used to control the working condition of the atomizer assembly 120. The controller 160 includes an airflow sensor and processor (not shown). The controller 160 triggers the opening and closing of the switch of the airflow sensor by sensing the size of the airflow, and further controls the working condition of the atomizer assembly 120. The different atomization can be gained by different suction force, which can improve the user's experience.

The bottom cover 170 is fixed to an end of the second housing 152. Preferably, the bottom cover 170 is fixed to the second housing 152 by laser welding to form a sealed connection. The bottom cover 170 is made of plastic material.

The assembly process of the electronic cigarette 100 is described as follows: first of all, the second conductive tube 134 is inserted to the first conductive tube 132 and then disposed to a plastic mold to form the first sleeve 136 by injection molding. The first conductive tube 132 and the second conductive tube 134 are tightly connected by the first sleeve 136. The spiral heating element 124 is disposed in the pipeline 1262 of the conducting liquid tube 126, and then the conducting liquid tube 126 is received in the receiving channel 1224 of the liquid reservoir 122, and the two wires 125 on the two ends of the heating coil are connected to the first conductive tube 132 and the second conductive tube 134, respectively; then the first housing 114 is inserted. The first housing 114 and the first sleeve 136 are fixed by laser welding. The liquid reservoir 122 is filled with liquid. The mouthpiece cover 112 is covered; the mouthpiece cover 112 is fixed to the first housing 114 by laser welding for sealing and connecting. The flexible conductive ring 114, the electrode head 154, the electrode holder 156, the spring 157, and the fixing base 158 are received in the second housing 152. The second conductive tube 134, the flexible conductive ring 114, and the second housing 152 cooperatively form a electrode, the first conductive tube 132, the electrode head 154, and the electrode holder 156 cooperatively form the other electrode, the positive and negative electrodes are connected to the heating element 124 and the battery 159, respectively; then the controller 160 is disposed in the second housing 152 and connected to corresponding elements to control the atomizer assembly 120. The first housing 114 is fixed to the second housing 152 together by laser welding. Finally, the base cover 170 is covered to form an electronic cigarette 100.

In use, the airflow enters the electronic cigarette 100 from the air intake 123, then the atomizer assembly 120 is controlled by the controller 160 to start work; the liquid stored in the liquid reservoir 122 is atomized to form smoke, the smoke passes through the air passage 116 and flow out from the air outlet 113.

In the foregoing electronic cigarette, the heating element is a heating tube capable of absorbing liquid, or a spiral heating coil disposed in the conducting liquid tube, the spiral direction of the heating coil is the same as the direction of the pipeline of the conducting liquid tube. The number of the heating coil can be significantly increased compared to the conventional heating coil. The contact area is enlarged, thus the atomization is improved. And there is no need to provide a support to support the heating element, thus the structure is simplified. The heating element is connected to the power assembly via the first connecting assembly and the second connecting assembly. The first connecting assembly and the second connecting assembly are cooperated to each other, the whole structural stability is great, the conductive elements have a larger contact area, and the conductive elements are connected by elastic elements, the structural stability is great, the position of each component is not easy to change, thus it has excellent electrical conductivity. The phenomenon of circuit break is avoided in use. Further, the junctions of the electronic cigarette where is easily loosened are fixed by laser welding, the structural stability is further improved and the sealing is great, the leakage problem of the electronic cigarette is completely solved. The various components are inserted together or formed by injection molding, the assembly process is simple. Accordingly, both the overall structural stability and the overall tightness of the electronic cigarette are very excellent. The phenomenon of contact failure is avoided, thus the electronic cigarette has a long service life.

Although the subject matter has been described in language specific to structural features, it is to be understood that the subject matter defined in the appended claims is not necessarily limited to the specific features described above. Rather, the specific features described above are disclosed as example forms of implementing the claims. Numerous modifications and alternative arrangements can be devised without departing from the spirit and scope of the described technology.

What is claimed is:

1. An electronic cigarette, comprising:
   a mouthpiece having a first housing, wherein the first housing defines an air passage therein;
   an atomizer assembly received in the first housing, wherein the atomizer assembly comprises a liquid reservoir and a heating element, and the liquid reservoir surrounds the heating element;
   a first connecting assembly received in the first housing, the first connecting assembly comprising:
      a first conductive tube and a second conductive tube connected to the heating element, wherein the second conductive tube is sleeved on the first conductive tube; and
      a first sleeve comprising an insulation tube, a convex ring, and a connecting portion, wherein the insulation tube is disposed between the first conductive tube and the second conductive tube; the convex ring is sleeved on the second conductive tube and fixed to an inner wall of the first housing; the connecting portion extends through a wall of the second conductive tube and interconnects the insulation tube and the convex ring; the convex ring and the second conductive tube define a receiving groove therebetween;
   a second connecting assembly comprising:
      a second sleeve, wherein the second sleeve is conductive and comprises a body and a boss protruding from the body, wherein the boss is received in the receiving groove; and
      a flexible conductive ring sleeved on the second conductive tube, wherein the flexible conductive ring comprises a clamping end and a contact end connected to the clamping end; the clamping end abuts against an inner wall of the second sleeve, the contact end comprises a plurality of resilient contacts, the second conductive tube is clamped by ends of the resilient contacts; and
   a power assembly comprising a second housing and a battery received in the second housing; wherein the second housing is fixed to the first housing; an end of the battery is electrically connected to the second sleeve, the other end of the battery is electrically connected to the first conductive tube.

2. The electronic cigarette according to claim 1, wherein an end of the convex ring has a first correction slope, an end of the boss has a second correction slope, the second correction slope and the first correction slope are mutually cooperated to each other.

3. The electronic cigarette according to claim 1, wherein a length of the second conductive tube is smaller than a length of the first conductive tube, an end of the second conductive tube and an end of the insulation tube cooperatively form a flange, an end of the atomizer assembly abuts against the flange.

4. The electronic cigarette according to claim 1, wherein a central axis of the first conductive tube and a central axis of the second conductive tube coincide with each other.

5. The electronic cigarette according to claim 1, wherein the plurality of resilient contacts are spaced apart from one another, each resilient contact is inclined to an axis of the clamping end, and a distance between two adjacent resilient contacts gradually decreases along a direction far away from the clamping end.

6. The electronic cigarette according to claim 1, wherein the contact end is shaped as a horn; the plurality of the resilient contacts are formed by defining a plurality of notches on the contact end.

7. The electronic cigarette according to claim 6, wherein the resilient contacts have a concave surface on an end abutting against the second conductive tube.

8. The electronic cigarette according to claim 1, wherein the power assembly further comprises an electrode head, an electrode holder, and a spring; an end of the electrode head is connected to the first conductive tube, the other end of the electrode head is received in the electrode holder; the spring is disposed between the electrode head and the electrode holder, an end of the spring abuts against the electrode head, the other end of the spring abuts against the electrode holder.

9. The electronic cigarette according to claim 8, wherein the first conductive tube has a concave surface on an end thereof, the electrode head has a convex surface on an end connected to the first conductive tube; the convex surface is in contact with the concave surface.

10. The electronic cigarette according to claim 8, wherein the power assembly further comprises a fixing base, an outer wall of the fixing base is fixed to the inner wall of the second sleeve; the electrode holder is received in the fixing base.

11. The electronic cigarette according to claim 1, wherein the liquid reservoir comprises a liquid medium, the heating element is a heating tube capable of absorbing liquid, at least partial inner surface of the liquid medium is in contact with an outer surface of the heating tube, an inside of the heating tube is communicated to the air passage.

12. The electronic cigarette according to claim 1, wherein the liquid reservoir and the heating element are provided with a conducting liquid tube therebetween, the conducting liquid tube has a channel formed therein communicated with the air passage, the heating element is a spiral heating coil; the heating coil is received in the pipeline, and the pipeline.

13. The electronic cigarette according to claim 1, wherein an inner wall of the conducting liquid tube defines a groove having a shape adapting to the heating coil, the heating coil is received in the groove.

14. The electronic cigarette according to claim 1, wherein the second housing is fixed to the first housing by a first weld ring.

15. The electronic cigarette according to claim 1, wherein the mouthpiece further comprises a mouthpiece cover; and the mouthpiece cover is welded to the first housing.

16. The electronic cigarette according to claim 1, wherein the convex ring is welded to an inner wall of the first housing.

* * * * *